(12) United States Patent
Kitani et al.

(10) Patent No.: US 8,287,518 B2
(45) Date of Patent: Oct. 16, 2012

(54) CONNECTING STRUCTURE FOR A CONNECTOR

(75) Inventors: Ichiro Kitani, Fukuroi (JP); Shigeaki Funamura, Fukuroi (JP)

(73) Assignee: Tyco Healthcare Group LP, Mansfield, MA (US)

( * ) Notice: Subject to any disclaimer, the term of this patent is extended or adjusted under 35 U.S.C. 154(b) by 433 days.

(21) Appl. No.: 12/195,030

(22) Filed: Aug. 20, 2008

(65) Prior Publication Data

US 2009/0062775 A1 Mar. 5, 2009

(30) Foreign Application Priority Data

Aug. 23, 2007 (JP) ................................. 2007-217264

(51) Int. Cl.
*A61M 25/16* (2006.01)

(52) U.S. Cl. ........ 604/539; 604/284; 604/533; 604/534; 604/535

(58) Field of Classification Search .................. 604/533, 604/284, 55, 523, 537, 539; 285/330, 333
See application file for complete search history.

(56) References Cited

U.S. PATENT DOCUMENTS

| 2002/0147429 | A1 | 10/2002 | Cowan et al. | |
| 2008/0306469 | A1* | 12/2008 | Masuda et al. | 604/535 |

FOREIGN PATENT DOCUMENTS

| DE | 4318101 | * | 8/1994 |
| EP | 1 872 824 | | 1/2008 |
| EP | 1 894 597 | | 3/2008 |
| JP | 05-031180 | | 9/1993 |
| WO | 2006/083333 | | 8/2006 |
| WO | WO 2007073939 A1 | * | 7/2007 |

OTHER PUBLICATIONS

EP Search Report dated Jan. 16, 2009.

* cited by examiner

*Primary Examiner* — Kevin C Sirmons
*Assistant Examiner* — Imani Hayman
(74) *Attorney, Agent, or Firm* — Lisa E. Winsor, Esq.

(57) ABSTRACT

A connecting structure for a connector in which a male-side connector and a merging pipe are connected by screwing together a female screw having protrusions formed on the inner peripheral surface of a lock ring and a male screw comprising protrusions formed on the outer peripheral surface of the merging pipe is provided with engaging recess parts on the female screw and engaging projections on the outer peripheral surface of the merging pipe which are able to engage with the engaging recess parts whereby when the male screw and the female screw are screwed together to reach an appropriate screwed state, the engaging protrusions engage with the engaging recess parts.

6 Claims, 3 Drawing Sheets

CONNECTING STRUCTURE FOR A CONNECTOR

TECHNICAL FIELD

The present invention relates to a connecting structure for a connector for connecting a male-side connector and a female-side connector.

BACKGROUND

Liquids such as drug solutions and blood are conventionally supplied to patients using a liquid transfusion line or a blood transfusion line provided with a tube. A connecting structure for a connector for connecting the various tubes which make up the liquid transfusion line or the like is used in such cases as for example, in Japanese Unexamined Patent Application Publication H5-31180, entirely incorporated by reference herein. This medical connecting instrument (connecting structure for a connector) is provided with a male connecting instrument which is connected to the ends of respective tubes which are connected to one another, and a female connecting instrument.

The male connecting instrument comprises a communicating pipe of which the tip end part constitutes the outer wall of a luer taper, and an outer cap which surrounds the communicating pipe. The female connecting instrument comprises a cylindrical body which can be inserted into the outer cap, and the communicating pipe can be fitted therein. Furthermore, a screw protrusion is formed on the inner wall of the outer cap, and a screw protrusion which can engage with the screw protrusion on the outer cap is formed on the outer wall of the female connecting instrument. Consequently, the male connecting instrument and the female connecting instrument can be connected in a state in which the communicating pipe is fitted inside the female connecting instrument by screwing the partner screw protrusions together while twisting the outer cap.

SUMMARY

A connecting structure for a connector is provided including a female screw having protrusions formed on an inner peripheral surface of a lock ring whereby a pipe body is in linking communication with a male-side connector, and a male screw having protrusions formed on an outer peripheral surface of a female-side connector screwed together and links in communication with a second pipe body wherein the pipe body and the second pipe body are linked in communication via the male-side connector and the female-side connector.

The connecting structure for a connector is configured for engaging recess parts cut out from a specific portion of either the female screw of the lock ring or the male screw of the female-side connector and which interrupt the protrusions of the female screw or the male screw. The connecting structure for a connector is also configured for engaging projections which engage the engaging recess parts provided on either the inner peripheral surface of the lock ring or the outer peripheral surface of the female-side connector, whereby when the male screw and the female screw are screwed together to reach an appropriate screwed state, the engaging projections engage with the engaging recess parts.

DETAILED DESCRIPTION

Figure 1:
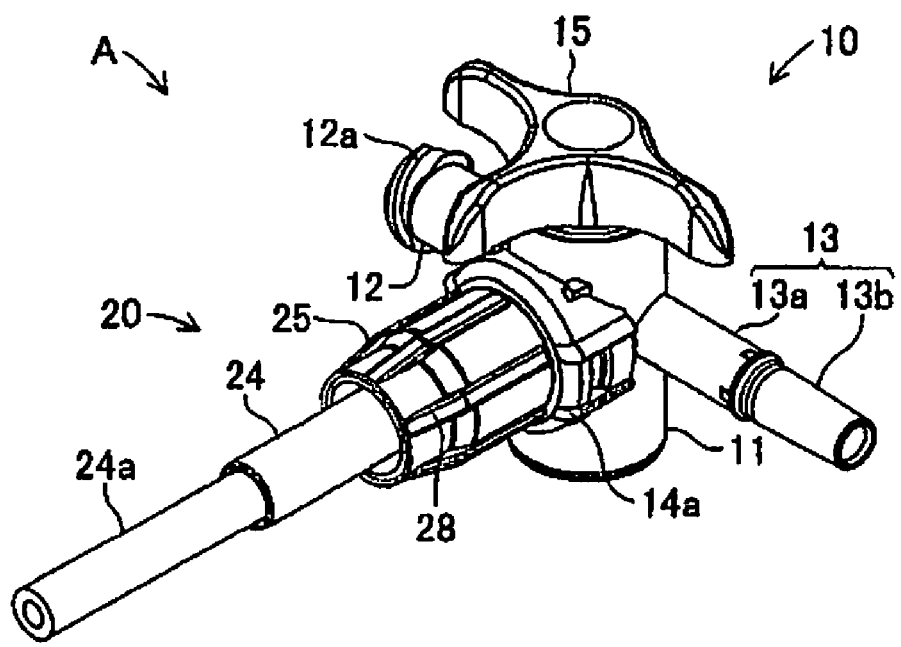
[FIG. 1] is an oblique view showing the connecting structure for a connector according to a mode of embodiment of the present invention.

However, with a conventional medical instrument as described above, cracks are produced in the female connecting instrument when the partner screw protrusions are fastened too tightly, and this causes leaks, while if they are not fastened tightly enough the connection between the male connecting instrument and the female connecting instrument is lost or the connection between the male connecting instrument and the female connecting instrument is loosened, which creates a gap between the two, and the liquid flowing inside may leak.

The present invention has been devised in view of the situation described above, and it aims to provide a connecting structure for a connector with which it is possible to prevent the appearance of cracks and liquid leakage.

In order to achieve the aim described above, the structural features of the connecting structure for a connector according to the present invention lie in the fact that it is a connecting structure for a connector in which a female screw comprising protrusions formed on the inner peripheral surface of a lock ring with which a male-side connector linking in communication with one pipe body is provided, and a male screw comprising protrusions formed on the outer peripheral surface of a female-side connector which links in communication with another pipe body are screwed together, whereby the one pipe body and the other pipe body are linked in communication via the male-side connector and the female-side connector, in which connecting structure for a connector provision is made for engaging recess parts which are cut out from a specific portion of either the female screw of the lock ring or the male screw of the female-side connector and which interrupt the protrusions making up the female screw or the male screw, and also engaging projections which can engage with the engaging recess parts are provided on either the inner peripheral surface of the lock ring or the outer peripheral surface of the female-side connector, and when the male screw and the female screw are screwed together to reach an appropriate screwed state, the engaging projections engage with the engaging recess parts.

With the connecting structure for a connector according to the present invention as described above, a male luer part is provided on the male-side connector, and a female luer part which can mate with the male luer part is provided on the female-side connector. Furthermore, a "lock ring" in the present invention is a fastening member which is placed on the outer periphery of the male luer part and comprises an annular or cylindrical portion for maintaining a communicating link between the male luer part and the female luer part by engagement with the female-side connector. Consequently, when the male-side connector and the female-side connector are connected, the male luer part is inserted into the female luer part, and the male screw and the female screw are screwed together by rotating the lock ring with respect to the female-side connector, whereby the male-side connector and the female-side connector can be connected in a state in which the female luer part and the male luer part are linked in communication. Then, when the male screw and the female screw are in an appropriate screwed state, the engaging projections and the engaging recess parts engage.

In this way, when the female screw of the lock ring is screwed together with the male screw of the female-side connector and the engaging projections reach the position of the engaging recess parts, the engaging recess parts and the engaging projections engage without further action. Consequently, the engaging projections and the engaging recess parts engage smoothly. An "appropriate screwed state" in this case is a state in which the fastening condition of the male screw and the female screw is neither too tight nor too loose, but at a suitable tightness, and furthermore in which there is no liquid leakage between the male-side connector and the female-side connector. Accordingly, when the engaging projections and the engaging recess parts have engaged, further rotation of the lock ring with respect to the female-side connector is stopped, whereby the male screw and the female screw are not fastened too tightly, so no cracks are produced in the female-side connector and the lock ring, and the male screw and the female screw are not fastened too loosely, creating a gap between the male-side connector and the female-side connector, so there is no leakage of drug solution from the gap.

Furthermore, when the male-side connector and the female-side connector are connected, the engaging projections and the engaging recess parts engage, and therefore the male-side connector and the female-side connector are not loosely connected when liquid is flowing from one pipe body to the other pipe body. In other words when the engaging projections and the engaging recess parts are engaged, the engaging projections are positioned between the end parts of protrusions configuring the female screw which have been cut away to create interruptions. Consequently, when an effort is made to rotate the lock ring with respect to the female-side connector in the direction to loosen the screwing of the male screw and the female screw, the engaging projections abut the end parts of the protrusions, and the screwing of the male screw and the female screw is prevented from being loosened. Moreover, if the lock ring is rotated in the direction to loosen the screwing of the male screw and the female screw with more than a certain amount of force, the lock ring rotates with respect to the female-side connector.

Furthermore, another structural feature of the connecting structure for a connector according to the present invention lies in the fact that the engaging recess parts are provided on the female screw, and the engaging projections are provided on the outer peripheral surface of the female-side connector. This means that the lock ring and the female-side connector can be integrally moulded in a simple manner.

A further structural feature of the connecting structure for a connector according to the present invention lies in the fact that the engaging projections are formed adjacent to the male screw. This means that it is possible to make the length of the female screw formed on the lock ring the same as or less than the length of the male screw formed on the female-side connector. When the engaging projections are provided further to the base end side than the male screw on the outer peripheral surface of the female-side connector, the female screw formed on the lock ring then needs to be provided up to a portion corresponding to a portion where the male screw is not formed. In other words, in order to form the engaging recess parts which engage with the engaging projections, it is necessary for the female screw to be provided running as far as a portion corresponding to a portion where the male screw is not formed, but when the engaging projections are formed adjacent to the male screw, it is unnecessary to provide the female screw in such a portion.

A further structural feature of the connecting structure for a connector according to the present invention lies in the fact that the engaging recess parts are provided on a portion of the female screw at the tip-end opening side of the lock ring, and the engaging recess parts and the engaging projections engage at the tip-end opening portion of the lock ring.

This means that when the female screw of the lock ring is screwed together with the male screw of the female-side connector, the engaging projections engage with the engaging recess parts at the tip-end opening side of the lock ring immediately before the end of the screwing operation. At this time, the engaging projections lie in a position slightly inside the tip-end opening of the lock ring. Accordingly, when the male screw and the female screw are screwed together, the length of the portion of the female screw which the engaging projections are in contact with or interfere with is only small, and it is possible to prevent the engaging projections and the female screw from becoming worn down or damaged, even with repeated attaching and detaching operations of the female-side connector and the lock ring. In this case, the engaging recess parts move a long distance along the male screw, but neither of them gets worn down or damaged because there is no contact between the engaging recess parts and the male screw.

Furthermore, the connecting structure for a connector according to the present invention offers an advantage in that the female screw of the lock ring and the male screw of the female-side connector can be formed in a simple manner. For example, when the engaging recess parts are provided inside the inner peripheral surface of the lock ring and the engaging projections are provided at the tip end side on the outer peripheral surface of the female-side connector, the engaging projections come into contact with the female screw or they move a long distance along the female screw in the vicinity of the female screw while the male screw and the female screw are being screwed together. Consequently, the engaging projections need to be formed accurately in a suitable position so as not to obstruct the screwing of the female screw and the male screw. As in the present invention, the engaging projections and the engaging recess parts are engaged at the tip-end opening side of the lock ring, so there is no need to give special consideration to this point.

A further structural feature of the connecting structure for a connector according to the present invention lies in the fact that the engaging recess parts are provided at a plurality of locations intersected by the female screw and specific imaginary lines which run in the axial direction of the lock ring on the inner peripheral surface of the lock ring. By means of this, the engaging projections can engage with a certain engaging recess part for each advance of a specific distance made by the male screw as it is screwed together with the female screw. Consequently, when the engaging projections are loosely engaged with the engaging recess parts at the start of engagement, the engaging projections engage with the following engaging recess part, and it is possible to cause the engagement of the engaging projections with the engaging recess parts so as to be engaged in an appropriate state. Furthermore, a plurality of engaging recess parts are disposed along the axis of the lock ring on the inner peripheral surface of the lock ring, and therefore the engaging recess parts have a simple shape.

In addition, with the connecting structure for a connector according to the present invention, the engaging recess parts can be provided on the male screw of the female-side connector, and the engaging projections can be provided on the inner peripheral surface of the lock ring. In this case, the engaging projections can be formed adjacent to the female screw. Furthermore, the engaging recess parts can be provided at a plurality of locations intersected by the male screw and specific imaginary lines which run in the axial direction of the female-side connector on the outer peripheral surface of the female-side connector.

Figure 2:
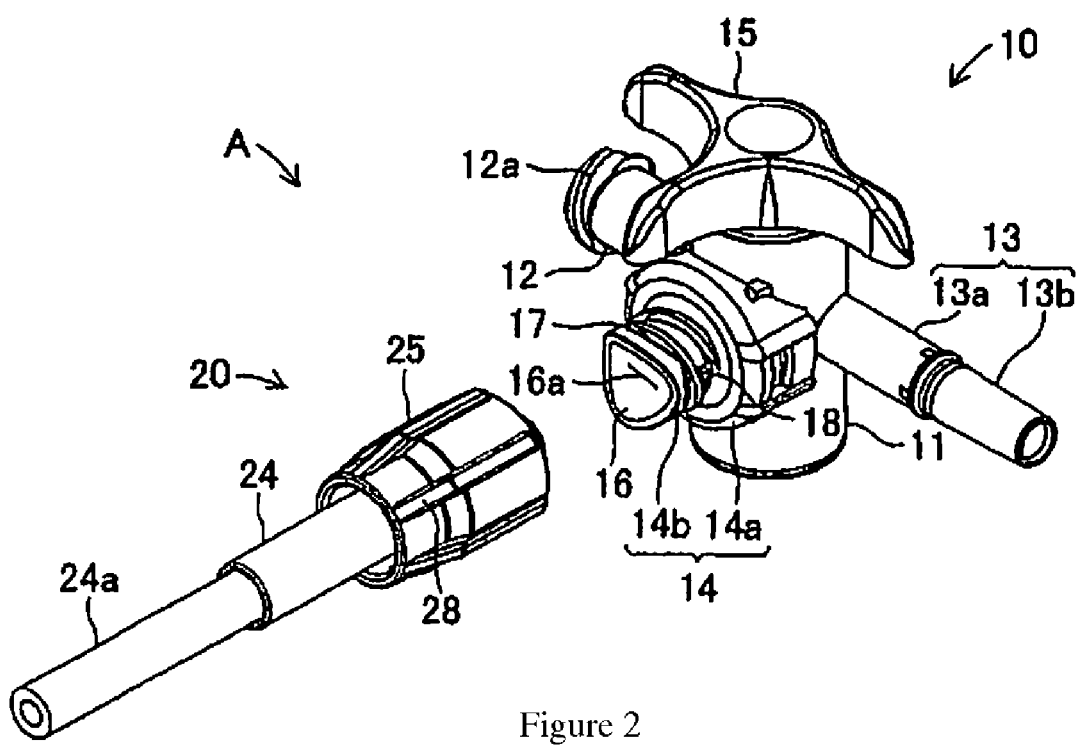
[FIG. 2] is an oblique view showing a state in which the male-side connector has been disconnected from the three-way stopcock of the connecting structure for a connector.
Figure 3:
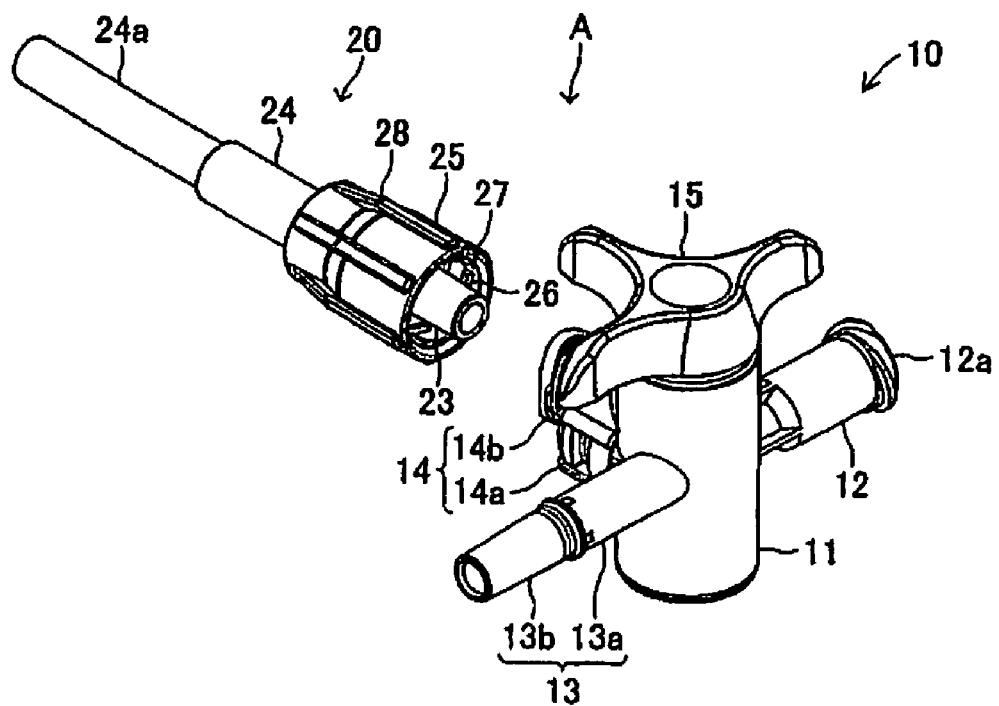
[FIG. 3] is an oblique view showing the state of the connecting structure for a connector of FIG. 2 seen from a different direction.

A detailed description of a connecting structure for a connector according to one mode of embodiment of the present invention will be given below with reference to the figures. FIGS. 1 to 3 show a connecting structure A for a connector, according to this mode of embodiment. This connecting structure A for a connector is incorporated in a liquid transfusion line for supplying a drug solution or the like to a patient's body, and it comprises a three-way stopcock 10 which acts as the female-side connector according to the present invention, and a male-side connector 20 which is detachably connected to the three-way stopcock 10. The three-way stopcock 10 allows a drug solution or the like sent from a container (not depicted) such as a drip tube housing a drug solution or the like, via a tube, to flow to a tube (not depicted) which is connected to the downstream side, and also inhibits this flow, and it also allows other drug solutions or the like sent from a container housing other drug solutions or the like, via the male-side connector 20, to flow to a tube which is connected to the downstream side, and also inhibits this flow.

The three-way stopcock 10 is configured by a cylindrical chamber part 11, an upstream pipe 12, a downstream pipe 13 and a merging pipe 14, these being respectively linked to the outer peripheral surface of the chamber part 11, and a flow channel switching part which is disposed between the inside and the outside of the chamber part 11 (only an operating part 15 which includes the flow channel switching part is depicted in the figures). In the state shown in FIGS. 1 and 2, the chamber part 11 comprises a cylindrical body which has a bottom, disposed so that the axial direction is vertically oriented, and where the lower end part is closed. The upstream pipe 12 is then joined to one of the outer peripheral surfaces of the chamber part 11, and a flow channel which links in communication with the inside of the chamber part 11 is formed inside said upstream pipe 12. Furthermore, the downstream pipe 13 is joined to the other outer peripheral surface of the chamber part 11, and a flow channel which links in communication with the inside of the chamber part 11 is formed inside said downstream pipe 13.

The merging pipe 14 is joined between the portion of the outer peripheral surface of the chamber part 11 where the upstream pipe 12 is joined, and the portion where the downstream pipe 13 is joined, maintaining an angle of 90° with respect to both the upstream pipe 12 and the downstream pipe 13. A portion inside the upstream pipe 12 on the chamber part 11 side configures the flow channel for allowing the passage of liquid, and a portion inside the upstream pipe 12 on the opening side configures the tapered fitting hole which becomes steadily larger in diameter nearer the opening. In other words, a male luer part which is provided at the end part of the tube is fitted to the opening-side portion of the upstream pipe 12. A screw part 12a for joining the male luer part to the upstream pipe 12 is then formed on the outer peripheral surface of the opening part of the upstream pipe 12.

The downstream pipe 13 comprises a base end part 13a which lies on the side of the chamber part 11, and a male luer part 13b which lies on the tip end side of the base end part 13a, and which is narrower than the base end part 13a. Furthermore, the male luer part 13b is formed with a tapering shape in which the tip end portion is narrower than the base end part 13a portion. The male luer part 13b is fitted to a female luer part which is provided at the upstream end of the tube which acts as the other pipe body according to the present invention. The merging pipe 14 comprises a large diameter base end part 14a positioned on the chamber part 11 side which is short in the axial direction and of large diameter, and a connecting part 14b which is provided at the tip end of the large diameter base end part 14a and is of smaller diameter than the large diameter base end part 14a.

Furthermore, a rubber stopper 16 is fitted into the connecting part 14b at a portion where it acts as a female luer part. This rubber stopper 16 consists of an elastic member made of natural rubber, synthetic rubber or elastomer etc. The rubber stopper 16 is then provided with a slit 16a which passes between the inside of the merging pipe 14 and the outside of the merging pipe 14 so as to form part of a flow channel in the merging pipe 14. Said slit 16a assumes a state in which it is closed due to the elasticity of the rubber stopper 16 when the flow channel in the merging pipe 14 is not being used.

Furthermore, when the flow channel in the merging pipe 14 is being used, the male luer part 23 of the male-side connector 20 which will be described below is inserted into the slit 16a of the rubber stopper 16, which enables the male-side connector 20 to link in communication with the inside of the chamber part 11. At this time, a sealed state is achieved between the male luer part 23 and the circumferential surface of the slit 16a due to the elasticity of the rubber stopper 16. Furthermore, a male screw 17 consisting of a protrusion is formed on the outer peripheral surface of the connecting part 14b between the tip end side of the connecting part 14b and the large diameter base end part 14a, and the engaging recess parts 18 comprising small protrusions are formed in the vicinity of the large diameter base end part 14a of the male screw 17.

The flow channel switching part comprises a valve body (not depicted) which lies inside the chamber part 11, and an operating part 15 which is joined to the upper end of the valve body and is provided with three parts which extend in three directions at intervals of 90°. The valve body rotates about the axis of the chamber part 11 by rotation of the operating part 15. Furthermore, two groove parts of different shape are formed on the outer peripheral surface of the valve body, and by rotating the valve body it is possible to form flow channels between the two groove parts and the inner surface of the chamber part 11 according to this angle, which flow channels link in communication or block the upstream pipe 12, downstream pipe 13 and merging pipe 14, respectively.

Figure 4:
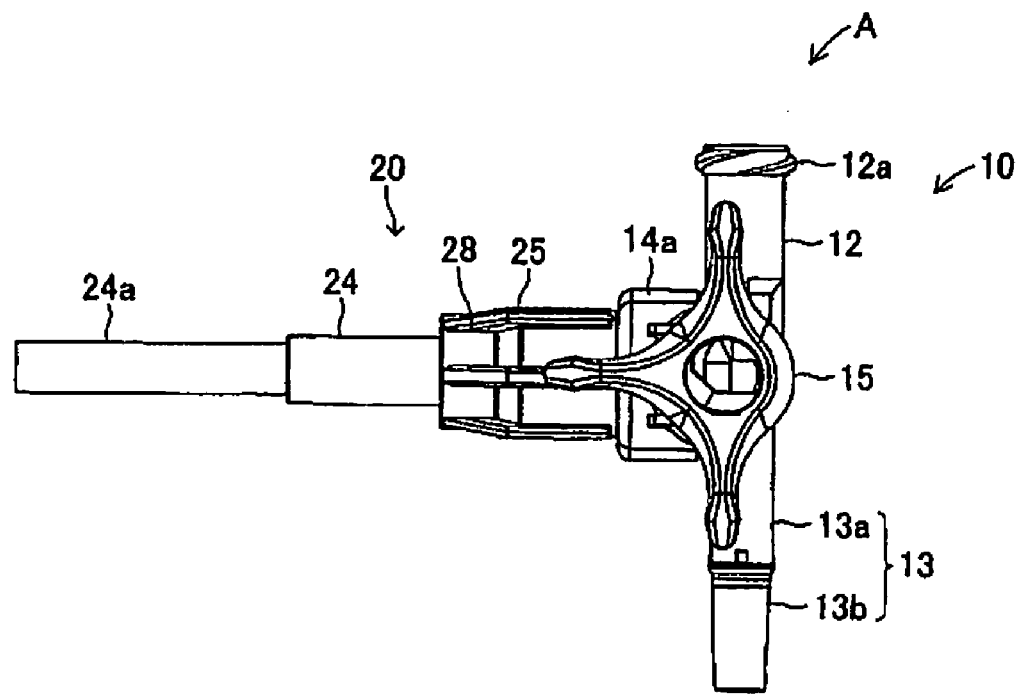
[FIG. 4] is a plan view of the connecting structure for a connector.

As shown in FIG. 4, for example, when the respective directions in which each of the parts of the operating part 15 extend match the upstream pipe 12, downstream pipe 13 and merging pipe 14, the upstream pipe 12, downstream pipe 13 and merging pipe 14 are all linked in communication. Furthermore, from the state in FIG. 4, when the operating part 15 is rotated through 90° anti-clockwise, and the directions in which two of the parts of the operating part 15 extend match the downstream pipe 13 and the merging pipe 14, respectively, with the remaining part positioned outside of the three-way stopcock 10, the downstream pipe 13 and the merging pipe 14 are linked in communication.

Then, from this state, a configuration is adopted so that when the operating part 15 is rotated through a further 90° anti-clockwise, and the directions in which two of the parts of the operating part 15 extend match the upstream pipe 12 and the downstream pipe 13, respectively, with the remaining part positioned outside of the three-way stopcock 10, the upstream pipe 12 and the downstream pipe 13 are linked in communication. In this way it is possible to link in communication or block the upstream pipe 12, downstream pipe 13 and merging pipe 14, respectively, by rotating the operating part 15 to rotate the valve body. Moreover, a reverse-flow prevention wall or the like is provided inside the chamber part 11, and this prevents drug solution or the like from flowing to the upstream pipe 12 or merging pipe 14 side from the downstream pipe 13 side, even if the upstream pipe 12 or the merging pipe 14 is linked in communication with the downstream pipe 13.

Figure 5:
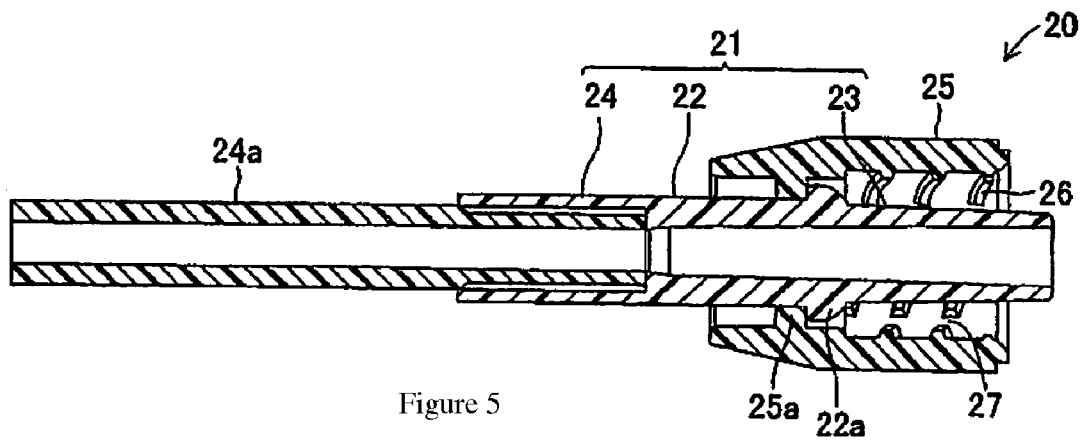
[FIG. 5] is a cross-sectional view of the male-side connector.

As shown in FIG. 5, the male-side connector 20 is configured by a male-side connector main body 21 which is formed as stepped cylinder, and a lock ring 25 which is attached to the outer periphery of the male-side connector main body 21 and is able to rotate about the axis with respect to the male-side connector main body 21, and also which is axially mobile. The male-side connector main body 21 is configured by a support part 22 which is centrally positioned in the axial direction of the male-side connector main body 21 and has a thick cylindrical shape, a cylindrical male luer part 23 which extends away from the tip end part of the support part 22 and is formed to be thinner than the support part 22, and a cylindrical connecting part 24 which extends rearwards from the base end part of the support part 22 and is formed to be thinner than the support part 22.

It should be noted that here, for ease of description, the right-hand side of the merging pipe 14 in FIGS. 1 and 2 is taken as the rear or the base end side, while the left-hand side is taken as the front or the tip end side, and the right-hand side of the of the male-side connector 20 in FIGS. 1 and 2 is taken as the front or the tip end side, while the left-hand side is taken as the rear or base-end side. The outer peripheral surface of the male luer part 23 is formed as a curved surface which tapers gently so that the diameter of the base end side is large, with the diameter becoming smaller towards the tip end side, and it is fitted into the slit 16a of the rubber stopper 16 which is fitted to the merging pipe 14 in a liquid-tight manner. The male luer part 23 is then fitted into the slit 16a of the rubber stopper 16, whereby the chamber part 11 of the three-way stopcock 10 and the male-side connector 20 are linked in communication.

Furthermore, the inner diameter of the support part 22 is set to be substantially the same as the inner diameter of the male luer part 23, and the outer diameter of the support part 22 is set to be greater than the outer diameter of the male luer part 23. A latch part 22a is then formed around the circumference on the outer periphery at the boundary between the support part 22 and the male luer part 23, in order to prevent the lock ring 25 from moving away from the male-side connector main body 21. The outer diameter of the connecting part 24 is substantially the same as that of the support part 22, and its inner diameter is greater than that of the support part 22 to the extent of their difference in thickness. The tip end part of the tube 24a is then engaged with the inside of the connecting part 24, whereby the male-side connector 20 is linked in communication with the tube 24a which acts as one of the pipes according to the present invention.

The lock ring 25 is formed with a substantially cylindrical shape which can house the connecting part 14b of the merging pipe 14 therein, and it is formed as a tapering curved surface in which the circumferential surface of the base end part side steadily tapers towards the rear. The size of said lock ring 25 is set so that the connecting part 14b of the merging pipe 14 can be inserted between it and the male luer part 23. A sliding engagement part 25a which can slide on the outer peripheral surface of the support part 22 and can also engage with the latch part 22a is formed along the circumference at a portion on the base end side of the inner peripheral surface of the lock ring 25. Consequently, the lock ring 25 can move in the axial direction of the male-side connector main body 21 and the tube 24 in a state in which it can be rotated in the axial direction with respect to the male-side connector main body 21, and also in which it is prevented from being withdrawn from the male-side connector main body 21.

Figure 6:
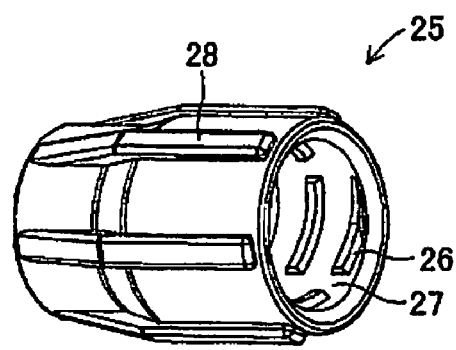
[FIG. 6] is an oblique view showing the lock ring.
Figure 7:
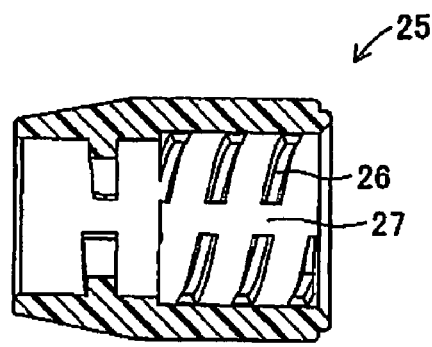
[FIG. 7] is a cross-sectional view of the lock-ring.

Furthermore, as shown in FIGS. 6 and 7, a female screw 26 comprising a plurality of protrusions which can be screwed together with the male screw 17 of the merging pipe 14 are intermittently formed between a portion whereby a certain distance is maintained from the tip end part of the inner peripheral surface of the lock ring 25 and a central portion in the axial direction. The areas between the parts of the female screw 26 are configured by a plurality of engaging recess parts 27 which can respectively engage with the engaging projections 18 formed on the outer peripheral surface of the merging pipe 14. These engaging recess parts 27 are formed at fixed intervals along the helix of the female screw 26. In other words, the engaging recess parts 27 are formed by cutting out the helical female screw 26 and forming those cut-out portions into a surface which is contiguous with the portion of the inner peripheral surface of the lock ring 25 where the female screw 26 is not formed.

Furthermore, the engaging recess parts 27 are provided with respective portions intersected by the helical female screw where it is not provided with engaging recess parts 27 and is continuous, and four imaginary lines running in the axial direction of the lock ring 25 on the inner peripheral surface of the lock ring 25. The four imaginary lines in this case are assumed lines which are set at portions spaced at 90° along the circumference of the inner peripheral surface of the lock ring 25. Consequently, the female screw 26 is configured by a plurality of protrusions which are interrupted for every 90° advance in the circumferential direction on the inner peripheral surface of the lock ring 25. Furthermore, when the male screw 17 of the merging pipe 14 and the female screw 26 of the lock ring 25 are screwed together, the engaging projections 18 engage with specific engaging recess parts 27 when the male screw 17 and the female screw 26 are in an appropriate screwed state (a state in which the screwed state is not too tight and not too loose).

Furthermore, when the engaging projections 18 have engaged with specific engaging recess parts 27, a catching sound is produced. By means of this, it is possible to confirm that the merging pipe 14 and the male-side connector 20 are joined in an appropriate state. Furthermore, when the engaging projections 18 and the engaging recess parts 27 have engaged, the engaging projections 18 are positioned between a certain two of the plurality of protrusions which make up the female screw 26. Consequently, it is not possible to screw the male screw 17 and the female screw 26 together with more force, and also the screwing between the male screw 17 and the female screw 26 does not come loose. Consequently, the join between the merging pipe 14 and the male-side connector 20 is maintained in an appropriate state.

Moreover, if the male screw 17 of the merging pipe 14 and the female screw 26 of the lock ring 25 are screwed together, and the screwed state of the male screw 17 and the female screw 26 when the engaging projections 18 have reached the first engagement recess part 27 becomes loose, the lock ring 25 is rotated without any other action, whereby the engaging projections 18 pass through the first engaging recess part 27, moving to the following engaging recess part 27. By repeating this, the engaging projections 18 engage with specific engaging recess parts 27. In this mode of embodiment, when the engaging projections 18 have engaged with the first engaging recess part 27, the screwed state of the male screw 17 and the female screw 26 is set to be appropriate. Furthermore, end-of-slide protrusions 28 with a fixed spacing between them in the circumferential direction and running in the axial direction are formed on the outer peripheral surface of the lock ring 25.

When a liquid transfusion line set provided with the connecting structure A for a connector configured in the manner described above is used, the male-side connector which is provided at the downstream end of a tube extending from a container which houses drug solution or the like is firstly connected to the upstream pipe 12 of the three-way stopcock 10. Furthermore, the female-side connector which is provided at the upstream end of a tube which has a piercing member such as an indwelling needle for piercing the patient's body so as to remain indwelling connected to its downstream end is connected to the downstream pipe 13. Next, the tip end of the male-side connector 20 is moved close and opposite to the tip end of the merging pipe 14 of the three-way stopcock 10, and the tip end of the male luer part 23 of the male-side connector 20 is pushed into the slit 16a of the rubber stopper 16.

Next, the tip end of the connecting part 14b of the merging pipe 14 is positioned inside the lock ring 25, and the male screw 17 and the female screw 26 come into contact, after which the lock ring 25 is rotated about a specific axis, whereby the male screw 17 and the female screw 26 screw together. Then, when the screwed state of the male screw 17 and the female screw 26 reaches an appropriate state, the engaging projections 18 of the merging pipe 14 and the engaging recess parts 27 of the lock ring 25 engage at the opening part side of the lock ring 25. By means of this, the merging pipe 14 and the male-side connector 20 link in communication in a state of linkage which is adequate for the purpose of preventing leakage of liquid. In this case, the lock ring 25 is prevented from retracting with respect to the three-way stopcock 10 because it cannot rotate with respect to the merging pipe 14 due to the engagement of the engaging projections 18 and the engaging recess parts 27.

Consequently, an appropriate screwed state is maintained between the male screw 17 and the female screw 26, without loosening of the screwing of the male screw 17 and the female screw 26. Furthermore, a container housing a drug solution or the like is connected to the upstream end of the tube 24a which is connected to the male-side connector 20. Then, when the drug solution or the like is supplied to the patient's body using the liquid transfusion line set, a piercing member at the downstream end of the tube which is connected to the downstream pipe 13 pierces the patient's body and remains indwelling. Next, the container at the upstream end of the tube which is connected to the upstream pipe 14 and the container at the upstream end of the tube 24a are opened, and a state is achieved whereby drug solutions or the like can be supplied from both containers. Then, by operating the operating part 15, specified drug solutions or the like are supplied to the patient's body in the required amounts.

As described above, with the connecting structure A for a connector according to this mode of embodiment, when the female screw 26 of the lock ring 25 is screwed together with the male screw 17 of the merging pipe 14, and the male screw 17 and the female screw 26 reach an appropriate screwed state, the engaging recess parts 27 provided on the lock ring 25 and the engaging projections 18 provided on the merging pipe 14 engage. In this case, the fastening condition of the male screw 17 and the female screw 26 is neither too tight nor too loose, but at a suitable tightness, and there is no leakage of drug solution between the male luer part 23 and the slit 16a of the rubber stopper 16. Accordingly, when the engaging projections 18 and the engaging recess parts 27 have engaged, further rotation of the lock ring 25 with respect to the merging pipe 14 is stopped, whereby the male screw 17 and the female screw 26 are not fastened too tightly, so no cracks are produced in the merging pipe 14 and the lock ring 25.

Furthermore, the male screw 17 and the female screw 26 are not fastened too loosely, creating a gap between the male luer part 23 and the slit 16a of the rubber stopper 16, so there is no leakage of drug solution from the gap. In addition, when an effort is made to rotate the lock ring 25 in the direction to loosen the screwing of the male screw 17 and the female screw 26, the engaging projections 18 abut the end parts of the protrusions, and the screwing of the male screw 17 and the female screw 26 is prevented from being loosened because the engaging projections 18 engage with the engaging recess parts 27, as they are positioned between the end parts of the protrusions which configure the female screw 26.

Furthermore, in this mode of embodiment, when the female screw 26 of the lock ring 25 is screwed together with the male screw 17 of the merging pipe 14, the engaging projections 18 engage with the engaging recess parts 27 at the tip-end opening side of the lock ring 25 immediately before the end of the screwing operation. At this time, the engaging projections 18 lie in a position slightly inside the tip-end opening of the lock ring 25, and therefore, when the male screw 17 and the female screw 26 are screwed together, the length of the portion of the female screw 26 which the engaging projections 18 are in contact with or interfere with is only small. As a result, it is possible to prevent the engaging projections 18 and the female screw 26 from becoming worn down or damaged, even with repeated attaching and detaching operations of the merging pipe 14 and the lock ring 25.

Furthermore, a plurality of engaging recess parts 27 are provided with a fixed spacing, and therefore the engaging projections 18 can engage with a certain engaging recess part 27 for each advance of a specific distance made by the male screw 17 as it is screwed together with the female screw 26. Consequently, when the engaging projections 18 are loosely engaged with the engaging recess parts 27 at the start of engagement, the engaging projections 18 engage with the following engaging recess part 27, and it is possible to cause the engagement of the engaging projections 18 with the engaging recess parts 27 so as to be engaged in an appropriate state. Furthermore, a plurality of engaging recess parts 27 are disposed regularly along the axis of the lock ring 25 on the inner peripheral surface of the lock ring 25, and therefore the engaging recess parts 27 have a simple shape.

Furthermore, the connecting structure for a connector according to the present invention is not limited to the mode of embodiment described above, and appropriate modifications can be implemented. For example, in the mode of embodiment described above, the engaging recess parts 27 are provided on the female screw 26 of the lock ring 25, and the engaging projections 18 are provided on the outer peripheral surface of the merging pipe 14, but the engaging recess parts may be provided on the male screw 17 of the merging pipe 14, and the engaging projections may be provided on the inner peripheral surface of the lock ring 25. Furthermore, in the mode of embodiment described above, the female-side connector consists of the three-way stopcock 10, and the merging pipe 14 and the male-side connector 20 are connected, but the upstream pipe 12 may be used as the female-side connector.

In this case, a male screw which is similar to the male screw 17 is provided on the outer periphery on the opening side of the upstream pipe 12, instead of the linking screw part 12a. In this case, the engaging projections are not limited to being provided adjacent to the female screw, and they may be provided at portions nearer to the chamber part 11 than the male screw on the periphery of the upstream pipe 12. In addition, the female-side connector need not be part of the three-way stopcock 10, and it may be configured by a single connector consisting only of a female-side connector. Further appropriate modifications within the technical scope of the present invention may also be made to other components of the connecting structure for a connector according to the present invention.

We claim:

1. A connecting structure for a connector, comprising:
a male-side connector including a male luer part, and a first pipe body in linking communication with the male-side connector;
a female-side connector including a female luer part and capable of mating with the male luer part, and a second pipe body in linking communication with the female-side connector, the second pipe body including a male screw formed on an outer peripheral surface thereof, the male screw having a plurality of protrusions, wherein a rubber stopper is fitted into the second pipe body at a portion where it acts as a female luer part, the rubber stopper having a slit which passes between the inside of the second pipe body and the outside of the second pipe body so as to form part of a flow channel in the second pipe body, such that when the flow channel in the second pipe body is in use, the male luer part of the male-side connector is inserted into the slit of the rubber stopper which enables the male-side connector to link in communication with the inside of a chamber attached to the second pipe body; and
a lock ring disposed on the outer peripheral surface of the male luer part, the lock ring including a female screw formed on an inner peripheral surface thereof, the female screw comprising an extruded helical path intersected by a plurality of recesses, such that when the male screw of the second pipe body and the female screw of the lock ring are screwed together, the recesses of the female screw of the lock ring engage with the protrusions of the male screw of the second pipe body when the male screw and the female screw are in an appropriate screwed state.

2. The connecting structure for a connector according to claim 1, wherein as the male luer part is inserted into the female luer part, the male screw and the female screw are screwed together by rotating the lock ring with respect to the female-side connector.

3. The connecting structure for a connector according to claim 1, wherein as the protrusions of the male screw engage with recesses of the female screw, a catching sound is produced.

4. The connecting structure for a connector according to claim 1, wherein the recesses are provided on a portion of the female screw at a tip-end opening side of the lock ring, and the engaging recess parts and the engaging projections engage at the tip-end opening portion of the lock ring.

5. The connecting structure for a connector according to claim 1, wherein the recesses are provided at a plurality of locations intersected by the female screw and specific imaginary lines which run in the axial direction of the lock ring on the inner peripheral surface of the lock ring.

6. A connecting structure for a connector, comprising:
a male-side connector including a male luer part, and a first pipe body in linking communication with the male-side connector;
a female-side connector including a female luer part and capable of mating with the male luer part, and a second pipe body in linking communication with the female-side connector, the second pipe body including a male screw formed on an outer peripheral surface thereof, the second pipe body further including a plurality of protrusions adjacent to the male screw; and
a lock ring disposed on the outer peripheral surface of the male luer part, the lock ring including a female screw formed on an inner peripheral surface thereof, the female screw comprising an extruded helical path intersected by a plurality of recesses, wherein the plurality of protrusions are configured to engage with one of the plurality of recesses at a time upon each advance of the male screw along the extruded helical path of the female screw as the male screw and the female screw are screwed together, and wherein each engagement between the plurality of protrusions and one of the plurality of recesses represents an appropriate screwed state in which the male screw and female screw are screwed together.

* * * * *